United States Patent [19]
Feld et al.

[11] Patent Number: 5,312,396
[45] Date of Patent: May 17, 1994

[54] PULSED LASER SYSTEM FOR THE SURGICAL REMOVAL OF TISSUE

[75] Inventors: Michael S. Feld, Waban; Irving Itzkan, Boston; Douglas Albagli; Joseph A. Izatt, both of Cambridge; Gary B. Hayes, Leominster; Richard Rava, Waltham, all of Mass.

[73] Assignee: Massachusetts Institute of Technology, Cambridge, Mass.

[21] Appl. No.: 644,202

[22] Filed: Jan. 22, 1991

Related U.S. Application Data

[63] Continuation-in-part of Ser. No. 578,645, Sep. 6, 1990, abandoned.

[51] Int. Cl.$^5$ .................. A61B 17/36; A61N 3/00
[52] U.S. Cl. ................................. 606/11; 606/2; 606/3; 606/7; 606/10; 606/13; 606/17; 607/88; 607/89; 607/94
[58] Field of Search ........................... 606/2-3, 606/7-11, 13-18, 128; 128/395-397; 607/88, 89, 90, 92, 93, 94

[56] References Cited

U.S. PATENT DOCUMENTS

| | | |
|---|---|---|
| 3,136,310 | 5/1964 | Meltzer . |
| 3,858,577 | 1/1975 | Bass et al. . |
| 4,072,147 | 2/1978 | Hett . |
| 4,207,874 | 6/1980 | Choy . |
| 4,418,688 | 12/1983 | Loeb . |
| 4,445,892 | 5/1984 | Hussein et al. . |
| 4,470,407 | 9/1984 | Hussein . |
| 4,564,011 | 1/1986 | Goldman . |
| 4,587,972 | 5/1986 | Morantte, Jr. . |
| 4,601,037 | 7/1986 | McDonald . |
| 4,641,912 | 2/1987 | Goldenberg . |
| 4,672,969 | 6/1987 | Dew .................................. 608/3 |
| 4,681,104 | 7/1987 | Edelman . |
| 4,682,594 | 7/1987 | Mok . |
| 4,791,927 | 12/1988 | Menger ................................ 606/3 |
| 4,830,460 | 5/1989 | Goldenberg . |
| 4,848,336 | 7/1989 | Fox et al. . |
| 4,862,886 | 9/1989 | Clarke et al. . |
| 4,887,600 | 12/1989 | Watson et al. .................... 606/15 |
| 4,913,142 | 2/1990 | Kittrell et al. . |
| 5,009,658 | 4/1991 | Damgaard-Iverson et al. ....... 606/3 |
| 5,139,494 | 8/1992 | Frieberg . |

FOREIGN PATENT DOCUMENTS 0144764 of 1984 European Pat. Off. .
0368512 of 1989 European Pat. Off. .
WO83/01893 of 1982 PCT Int'l Appl. .

OTHER PUBLICATIONS

Grundfest et al., "Pulsed Ultraviolet Lasers & The Potential for Safe Laser Angioplasty", Aug.-1985, all pages in document.

Fujii, et al., "Fibre Bundle Scanner for Laser Photocoagulation Treatment", Optics and Laser Tech., (Feb. 1982).

Abela et al., "Effects of Carbon Dioxide, Nd-YAG and Argon Laser Radiation on Coronary Atheromatous Plaques", Am. J. Cardiology, 50(6): 1199-1205 (1982).

Isner & Clarke, "The Current Status of Lasers in the Treatment of Cardiovascular Disease", IEEE J. of Quantum Elec., QE-20(12): 1406-1419, (1984).

Ginsburg, et al., "Percutaneous Transluminal Laser Angioplasty for Treatment of Peripheral Vascular Disease", Radiology, 156:619-624 (1985).

Murphy-Chutorian et al., "Selective Absorption of Ultraviolet Laser Energy by Human Atherosclerotic Plaque Treatment with Tetracycline", Am. J. of Cardiology, 55 (May 1985).

Isner & Clarke, "Lasers: Their Potential In Cardiovascular Medicine", Cardiovascular Med., (May 1985).

Lee et al., "Current and Potential Uses of Lasers in the Treatment of Atherosclerotic Disease", Chest, 85(3), (Mar. 1984).

Lane et al., "Ultraviolet Laser Ablation of Skin", Archives of Dermatology, (1984).

Primary Examiner—Randall L. Green
Assistant Examiner—P. Zuttarelli
Attorney, Agent, or Firm—Hamilton, Brook, Smith & Reynolds

[57] ABSTRACT

Removal of body tissue with a long pulsed lasers is achieved such that sufficient energy to remove tissue is transmitted to the desired body without damaging an optical fiber transmitting the laser radiation. Pairs of pulses having the same or different wavelengths are coupled to more effectively remove tissue from the surgical site.

20 Claims, 14 Drawing Sheets

PULSED LASER SYSTEM FOR THE SURGICAL REMOVAL OF TISSUE

Submitted herewith for filing is a Continuation-in-Part application of prior Ser. No. 07/578,645 filed Sept. 6, 1990.

BACKGROUND OF THE INVENTION

Surgical methods are being developed to ablate tissue by inserting an optical fiber catheter into a body lumen and passing laser light through the fiber optics onto the surgical site. Laser catheters employing optical fibers to deliver laser radiation to ablate tissue are coupled to pulsed Xe:Cl excimer or other suitably powered lasers. However, there are many problems associated with using excimer lasers with a wavelength of 308 nm, for example. Noxious gases used with excimer lasers must be vented. The laser is extremely large and bulky and generates an excessive amount of electrical noise that may affect other hospital equipment. As a consequence, excimer lasers require heavy shielding. Moreover, the laser beam quality is so poor that optical processing of the beam is difficult. Also, the excimer laser generates light in the UV-B range resulting in the potential for mutagenicity of the irradiated tissue. The use of such a system at a wavelength of 308 nm is known to cause cataracts. In view of the dangers associated with excimer lasers and other problems associated with other existing medical lasers, a need exists for the development of a surgical laser system more suitable for a hospital environment, that will provide a radiation source suitable for tissue ablation and provide a more convenient and reliable laser source for a variety of medical applications.

SUMMARY OF THE INVENTION

To avoid the problems associated with excimer lasers, we have chosen a solid state ND:YAG laser, frequency tripled to 355 nm, to ablate tissue. The pulses produced by currently available lasers such as ND:YAG, doubled alexandrite, or Ti:sapphire are short (approximately 100 ns or less) and at the energies required for ablation the use of optical fiber waveguides to deliver the radiation to tissue can result in damage to the optical fibers. Other laser host materials can be used, such as YALO, or yttrium aluminate. Also, other types of solid state lasers such as holmium doped lasers can be used. By providing a laser pulse of sufficient duration and energy from a solid state laser, tissue can be ablated without damaging the optical fiber used to deliver radiation to the surgical site. The laser output may be a single pulse or a plurality of pulses with a fluence, or energy/$cm^2$, sufficient to remove tissue. Moreover, the laser wavelength is preferably in the range of 320 to 400 nm.

The laser surgery techniques can be extended to all tissues of the body. For example, skin lesions can be excised by direct application of a laser beam without transmission through optical fibers. Similarly, a solid state laser beam can be used for the removal of cancerous or precancerous material during surgery. Also, a catheter can be used to apply the solid state laser beam to calcified material or soft tissue within a body lumen. Laser revascularization of coronary arteries utilizing solid state lasers can thus remove calcified plaque. Spectroscopic diagnostics are utilized to determine what tissue is to be removed. Moreover, in vitro applications are useful for biopsy and autopsy purposes.

In the preferred embodiment, the short pulse output of the solid state YAG laser is transmitted to an optical "extender" for "stretching" the initial pulse into a train of a selected number of pulses, each delayed by a given time interval, the train of pulses resulting in the "filling" in of overlapped pulses. Thus, pulses having a desired waveform can be lengthened by overlapping several pulses. When the interpulse delay is less than the initial, or seed pulse duration, the train of pulses overlap into a single pulse. When a plurality of initial, or seed pulses are received by the filler/multiplexer, the separation between the resulting output pulses are such that the pulse trains from the respective initial pulses do not overlap.

The optical extender utilizes beam splitters and mirrors to produce the desired pulse trains. Similarly, a pulse filler/multiplexer utilizes a selected number of different optical delay paths which are combined by beam splitters to produce the desired number of outputs. The positions of the pulse extender and pulse filler can be reversed to optimize particular operating conditions. Pulse duration is set such that tissue is removed without damaging the transmitting optical fibers.

In another preferred embodiment a solid state laser per se can be constructed to produce pulses having the desired duration, power and shape to remove tissue. For example, a slow Q switched, mode locked laser can be used to provide such a pulse. Also, two or more lasers can be used to produce pulses with the desired time separation between pulses from the respective lasers. Thus, with our invention, a system is provided for the precise laser machining of all human tissues.

A further embodiment of the present invention relates to the use of two or more colors or wavelengths of light to further increase the effectiveness of the tissue ablation process. In this procedure the removal of a selected region of tissue is initiated using a pulse of light of one wavelength and then completing the removal of the selected region by irradiating the same region with a second pulse of light of another wavelength.

The first pulse can produce transient or non-transient changes in the tissue. In the case of transient changes, the second pulse is delivered to the tissue within a period of time that is short enough to work in combination with the first pulse. It is by coupling the effects of two pulses of different wavelengths that has resulted in a substantial increase in ablation effectiveness.

The first pulse operates to prepare the tissue by thermal, photochemical, vibrational or electronic excitation mechanisms that either alone, or in combination, alter the absorption and/or scattering characteristics of the tissue relative to the second pulse of different wavelength. The precise mechanism by which the absorption and/or scattering characteristics of the tissue is altered is dependent upon the type of tissue, the pulse duration, temporal separation of pulse pairs, the wavelengths of the pulses and the energy delivered by each pulse to the tissue. Note that the first pulse can also produce some permanent non-reversible change that can be used to prepare the tissue. In this embodiment the temporal separation of the pulses is not as critical for effective two color ablation. Generally, this type of tissue preparation is photochemical in nature.

In one embodiment a ND:YAG laser produces single pulses each of which is divided into a first subpulse that is tripled (to 355 nm, for example) and delivered to arterial tissue, and a second pulse, at the fundamental frequency (1066 nm), that is delivered to the tissue through an optical delay to provide the desired pulse separation, within one microsecond of the first pulse. The first 355 nm pulse alters the propagation of light through the irradiated tissue such that the second pulse is more fully absorbed by the tissue and results in the removal of the desired amount of tissue. For the purposes of the present application, it is the use of the first pulse to increase the rate of attenuation of the second pulse as it propagates through the tissue that is critical to effective ablation.

DETAILED DESCRIPTION OF THE INVENTION

Figure 1:
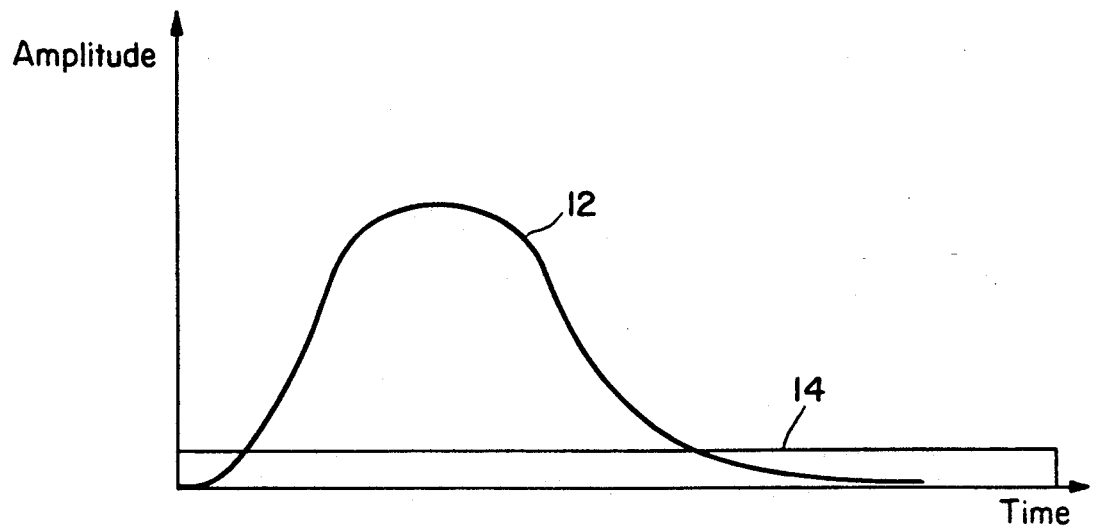
FIG. 1 illustrates the output pulse of a typical solid state laser relative to a preferred rectangular pulse.

FIG. 1 illustrates the typical pulsed output 12 of a solid state laser. The rectangular pulse 14 represents an optimal pulse configuration that can be approximated by the methods described below. The amplitude of pulse 14 is much less than the peak amplitude of output 12. Also, the peak height of pulse 14 is small relative to its time length duration. However, the areas under the respective curves 12 and 14 are comparable. When the duration of pulse 14 with the necessary fluence is sufficiently long and has the necessary energy density it provides an improved pulse configuration for the ablation of tissue. A wavelength of 355 nm is advantageous in that it produces a desirably small penetration depth in body tissue. Thus, by controlling the penetration depth with the appropriate selection of wavelength, damage to underlying healthy tissue is reduced. Moreover, ND:YAG lasers can be used safely in hospitals, have good beam quality, and operate at non-mutagenic wavelengths. However, Nd:YAG lasers generally produce only frequency tripled short pulses having the necessary ablation energy (of a duration approximately 10 ns) efficiently.

Solid state lasers can produce long duration pulses by using long, high-Q cavities or by appropriate Q switching techniques. However, it is difficult to produce a long duration pulse with a frequency tripled solid state laser. Since, it is often desirable to use optical fiber waveguides to deliver radiation to a surgical site, particularly at locations accessible through body lumens, long duration pulses are used with sufficient energy to remove tissue and which can pass through without damaging the bulk material or surface of that fiber.

Figure 2:
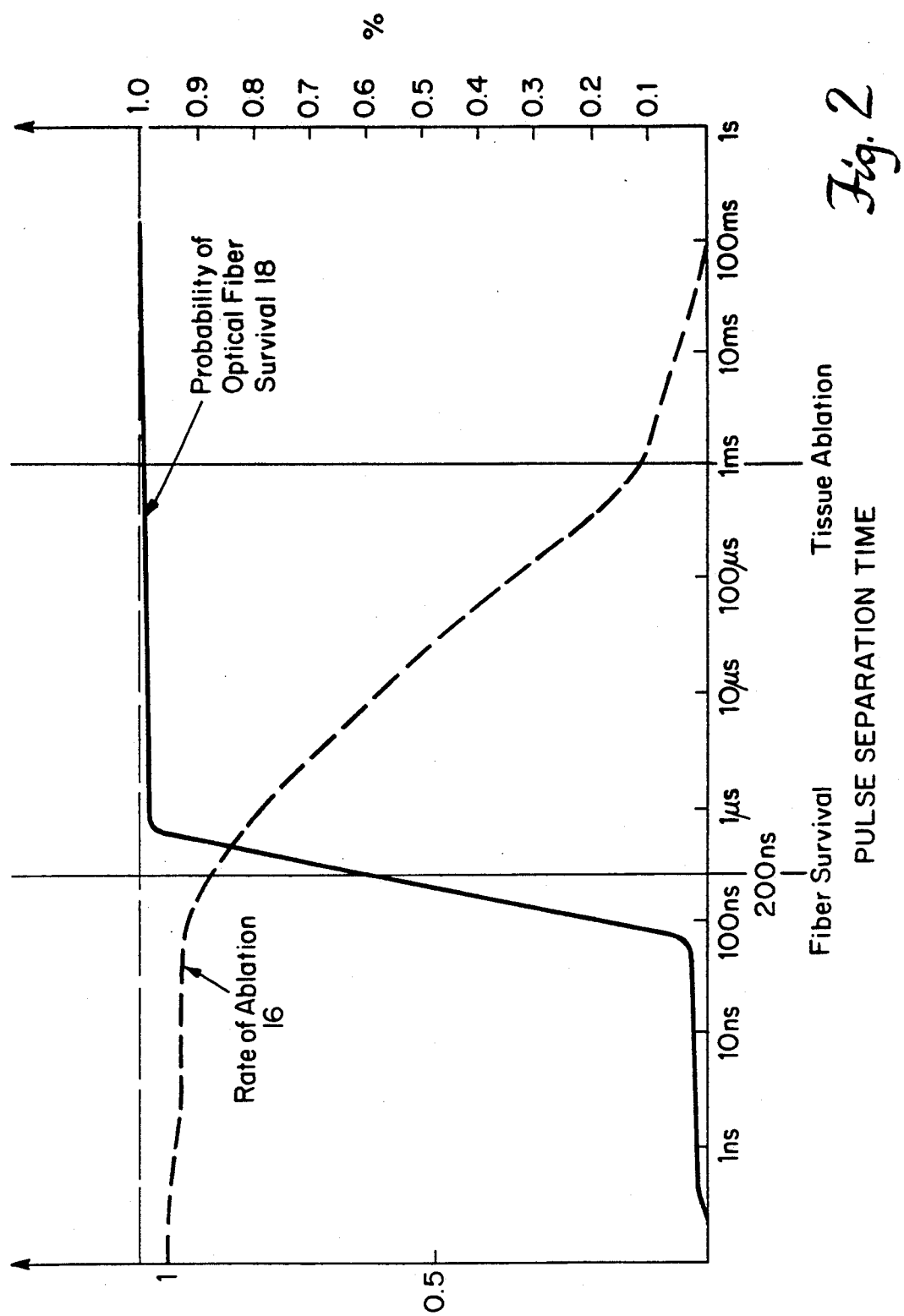
FIG. 2 illustrates the rate of tissue ablation and the probability of optical fiber survival as a function of pulse separation.

FIG. 2 illustrates the two conditions which must be met to transmit a satisfactory output pulse. First, sufficient energy must be transmitted to the body area to remove tissue. Second, the energy must be below the threshold of damage for the optical fiber. The respective materials were tested using two short pulses (7.5 ns) at a wavelength of 355 nm laser light of equal energy. The pulses were delayed by an amount varying from 1 nanosecond to 1 second.

The effect of various pulse delays on body tissue is shown by the dotted line in FIG. 2. The tissue effectively "remembers" that it has been irradiated for times in excess of several microseconds i.e., energy deposited in tissue can be stored for several microseconds and the energy needed to reach the ablation threshold is cumulative over this period. It has been found that the rate of ablation or crater depth is a maximum under these conditions for a pulse separation less than 100 nsec and decreases steadily to zero at 100 msec separation. However, effective ablation can generally occur at a pulse separation of less than 1 msec.

The selection of an appropriate combination of laser wavelength, pulse energy and pulse duration is critical to properly remove body tissue. The proper choice of laser pulse parameters is especially important for the removal of calcified plaque. It has been found that the most efficient removal of "hard" biological tissue occurs when wavelengths below 400 nm and intensities in the range of $MW/cm^2$ to $GW/cm^2$ are used. Accordingly, within these limits, the amount of tissue ablated depends primarily on fluence (energy/$cm^2$) and the same removal amount be obtained with long, low intensity pulses as with short, high intensity pulses.

We have determined that hard body tissue such as bone, tooth enamel and calcified plaque can be removed efficiently by vaporizing the soft tissue component inside the hard tissue which entrains and removes the hard component particles which are not vaporized. The boiling point of the soft component in the hard tissue is approximately 300° C. A fluence of $10^6$-$10^9$ Watts/$cm^2$ is required to vaporize the soft tissue. By comparison, the melting point of hard tissue is 1600° C. To vaporize the hard component would require a fluence which is substantially greater than $10^9$ Watts/$cm^2$. Thus, much less power is required to remove hard tissue using our method. Moreover, less damage is incurred to areas surrounding the surgical site by using our method of vaporizing the soft component of hard tissue without vaporizing the hard components. With our technique, plasmas are not created and less heat is transmitted to the areas surrounding the surgical site.

Also, ablation proceeds at a energy rate which is greater than the rate of thermal diffusion into the surrounding tissues. Thus, the fluence is maintained above the threshold required for tissue removal. Since the vaporization of soft tissue entrains heat away from the surgical site, the process results in a "cold cut" at the surgical site.

The determination of the requisite laser pulse parameters is extremely difficult in view of the previous lack of understanding of the nature of tissue response to laser light. The laser intensity should be great enough to vaporize the soft component in the hard tissue at a sufficiently rapid rate to entrain and remove the hard components which do not vaporize. Thus, the process requires less absorbed laser energy to remove a given amount of tissue, compared to ablation in which both tissue components are vaporized. Also, since the hot material is rapidly removed, much of the deposited heat is carried out of the tissue before it can be transferred to the adjacent tissue via thermal diffusion. The irradiance, fluence, and wavelength of a laser beam represent the fundamental controllable parameters governing the ablation process.

The effect on optical fibers involves a converse relationship. The exact path of curve 18 illustrating the probability of optical fiber survival is dependent on the power level employed. The instantaneous power in the optical fiber at any given time must be below the threshold which will cause damage. Note that the energy transmitted is directly related to the pulse duration. The damage to the optical fiber may occur when adjacent pulses overlap and breakdown thresholds are exceeded. However, optical fiber damage is rapidly reduced to a tolerable level at a pulse separation in the range of 100–200 nanoseconds. Two breakdown mechanisms predominate: self focusing and surface breakdown. Self focus damage limits peak power. Front surface breakdown restricts the pulse energy profile for a pulse energy to do ablation. Note also that the amount of energy which can be transmitted through a fiber is limited by damage of the fiber core due to electron avalanche breakdown. For shorter pulses or larger optical fiber cores, damage is caused by self focusing within the fiber core. For longer pulses or smaller optical fiber cores, damage is caused by front surface breakdown. Thus, optical fibers can only transmit high energy pulses at moderate power levels which require longer pulses.

To summarize, three requirements must be met. First, each fiber must transmit enough energy to ablate a required cross-sectional area exceeding the core diameter of the fiber. Second, peak power on each fiber must be below self focussing breakdown. Finally, the pulse energy profile on each fiber must be below the threshold for front surface breakdown. The energy required for ablation of tissue must be greater than thermal relaxation or heat dissipation at the removal site. FIG. 2 illustrates that pulse separation between 100–200 nanoseconds and 1 millisecond fulfill these requirements. By stretching the solid state laser pulse, we simply and effectively solve the mutual problems of tissue removal and optical fiber transmission. Various pulse trains and sequences of pulses with variable delays, in addition to continuous pulses can be utilized. A variety of pulse shapes can be used to increase the energy transmitted. For example, a weak first pulse with an energy below the ablation threshold can be transmitted to the surgical site, followed by a second pulse with much greater energy than the first, such that the cumulative fluence of the two pulses is sufficient to ablate tissue.

Our invention uses a pulse separation which is greater than the relaxation time of the avalanche process in the optical fiber. Thus, electron avalanche breakdown is avoided. Also, the pulse separation is less than the tissue memory, i.e., the time period during which the energy is stored. As a result, tissue is removed without damaging the optical fiber which transmits the laser pulse.

Figure 3:
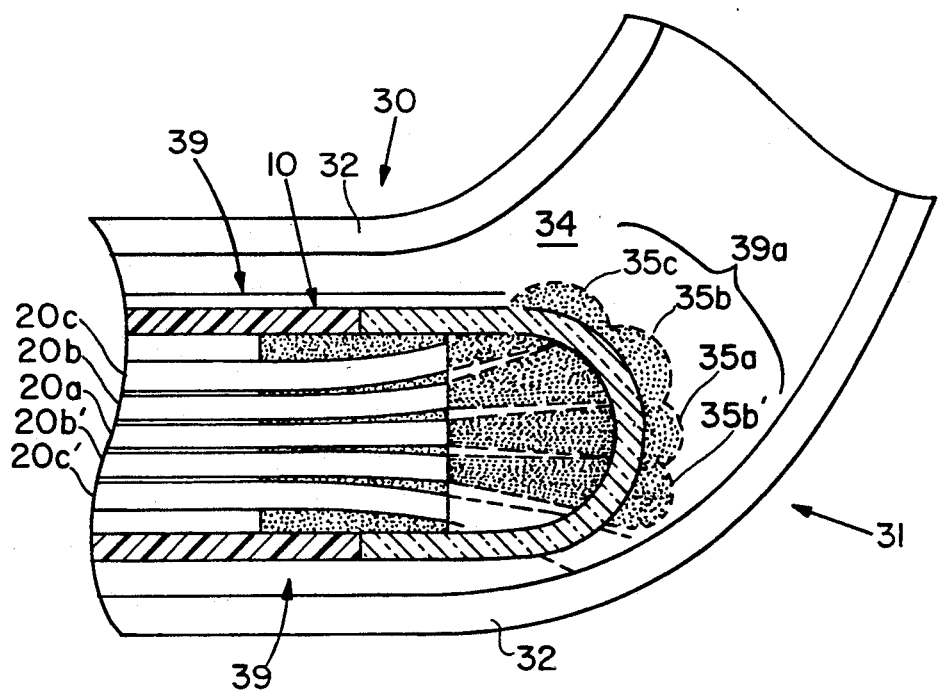
FIG. 3 is a sectional view of a laser catheter embodiment disposed in the bend of an artery and illustrating the device in operation.

FIG. 3 shows the typical catheter environment utilized to apply the laser light at a desired body part. This, catheter is described in detail in U.S. Pat. No. 4,913,142 to Kittrell et al. which is incorporated herein by reference. As noted in Kittrell et al., spectroscopic analysis is utilized to accurately position the catheter. The laser catheter 10 contains a set of optical fibers, consisting of a central optical fiber 20a, a first ring of optic fibers represented by 20b, b', and a second ring of optical fibers 20c, c'. Note that a central lumen can also be provided in another embodiment in which a guidewire is used to position the catheter. Each optical fiber is composed of a core, a cladding with a lower index material than the core, and a protective buffer. In the preferred embodiment the core and cladding are fused silica or glass or fluorite glass, so as to withstand high laser power. Catheter 10 is shown removing plaque 34 from within an artery 32. Laser light is applied to the optical fibers to remove overlapping nibbles 35a, b, b', and c as needed.

Figure 4:
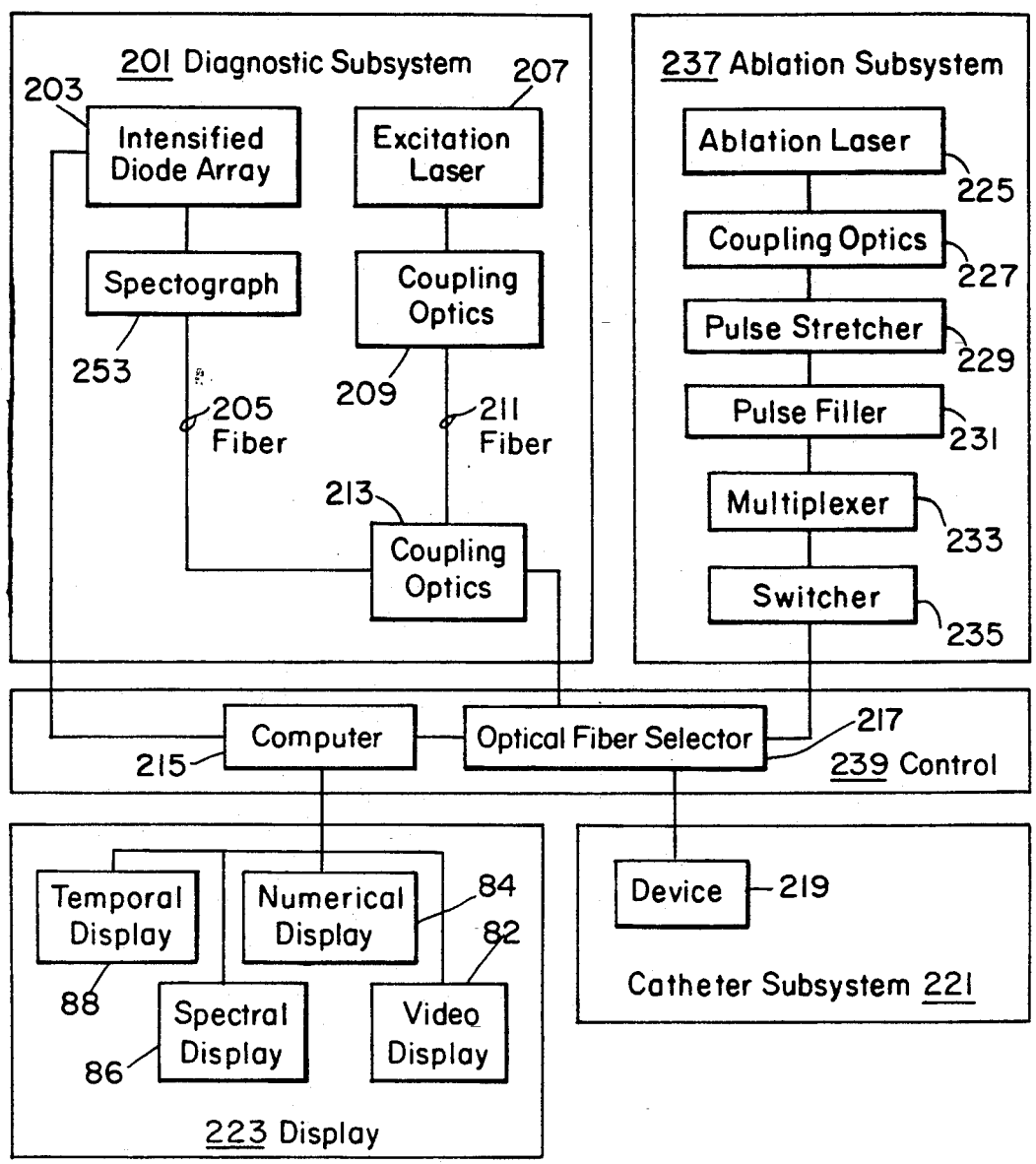
FIG. 4 is a block diagram of a system in accordance with the invention for removal of unwanted deposits in an artery.

FIG. 4 is a block diagram for the system of the invention which utilizes spectroscopic diagnosis for removal of plaque in an artery. The pulse stretcher 229 and the pulse filler/multiplexer 231, 233 produce an output sufficient to remove tissue. The pulse stretcher optically regenerates pulses. The pulse filler/multiplexer fills the space between the pulses. Again, note that the term "extender" refers to either "stretching" pulses or "filling" pulses or both. These elements can be interchanged in this optical circuit.

To remove plaque, laser catheter 219 with an optical shield is inserted into the artery and the distal end of the catheter is brought into contact with the lesion. Next, a determination is made as to the type of tissue at which each optical fiber 20a–c' is aimed. Only fibers aimed at diseased tissue are activated. Thus, selective tissue removal is obtained. Spectral diagnostics are used to diagnose the tissue in front of each fiber.

A laser light source 207, is applied to the fibers. The diagnostic light is sent to the fiber of choice by the optical fiber selector 217.

The diagnostic light exits the selected optical fiber and falls on the tissue. The tissue absorbs the light and a fraction of the absorbed light is re-emitted, usually at a longer wavelength. This light is returned to the optical fibers and exits from selector 217, and is detected by a photodiode, photomultiplier or other detector 203. Diagnostic subsystem produces the entire spectral signal which is coupled to computer 80.

The computer stores the information as a spectrum, which is a graph of light intensity vs. wavelength. This can be displayed immediately on the video display 82 or compared to an existing spectrum stored in the computer and the difference displayed on the spectral display 86. Temporal display 88 can display corrections made for the wavelength dependent sensitivities of the source. Information from either the temporal or spectral display can be stored in the computer 80. The comparative data is shown on numerical display 84 to provide a quantitative measure of the health of the tissue observed.

With a multichannel detector and a reasonably fast computer, or with appropriate multiple filters and detectors, it is possible to gather this information in a fraction of a second. Thus, a spectral or numerical display is provided which indicates the type of tissue at which the fiber of interest is aimed. If the tissue is plaque, and is to be removed, then fiber selector 217 will align this fiber with the output beam of the high power laser 225. Then, the high power laser 225 is turned on and an appropriate power level is selected for a predetermined amount of time to remove a certain amount of diseased tissue. The beam of laser 225 is transmitted to pulse stretcher 229 and pulse filler/multiplexer 231, 233 to properly adjust the beam fluence.

The procedure is repeated for different fibers. Where diseased tissue is detected, it is quickly removed. The laser catheter 10 nibbles away at the plaque, leaving the healthy artery wall intact.

If the artery 30 makes a bend 31 as shown by FIG. 3, the laser catheter 10 will tend to make contact with artery wall 32 at the outside wall of the bend. To prevent the catheter from contacting the artery wall, the optical fiber 20c is not fired. The lesion is removed asymmetrically. This allows the laser catheter 10 to follow the lumen 39, 39a around the bend. Thus, the artery wall 32 is not irradiated and is not perforated.

It should be noted that "stretching" refers to generating a train of pulses from an initial, or seed, pulse. Also, "filler/multiplexer" refers to generating several overlapped pulses to produce a solid pulse. The term "extender" encompasses both topics.

Control system 239 is effected, preferably with a 80386 IBM PC compatible computer 215. An imaging spectrograph 253 is fitted with a 200-line holographic grating to separate tissue autoflourescence transmitted by the transmission into its spectral components. An applied research 1420 intensified diode array 203, controlled by an applied research 1461 control interface as directed by the computer control system via an IEEE - 488 interface, is utilized to detect tissue autofluorescence at all wavelengths. An EGG Princeton applied research 1304 gate pulser drives the gate of the diode array intensifier as directed by the 1461 control interface. A custom timing interface provides an external clock running at 20 Hg to synchronize the pulse laser with the gate pulser and diode array control interface.

The short duration pulse from a solid state laser can be optically extended, i.e., stretched and/or filled. This concept of using a solid state laser to produce long pulses or alternatively stretching or sequencing pulses can be achieved in several embodiments. Two or more lasers could be used to produce several output pulses separated by at least 100 nanoseconds and combined using optical devices such as a Wollaston prism.

Also, a ND:YAG frequency tripled solid state laser can be used to generate long pulses to remove body tissue. A slow Q switched, mode locked long pulse laser can be used to develop a low intensity pulse of sufficient duration (i.e., adequate fluence) to remove tissue without damaging optical fibers.

Figure 5:
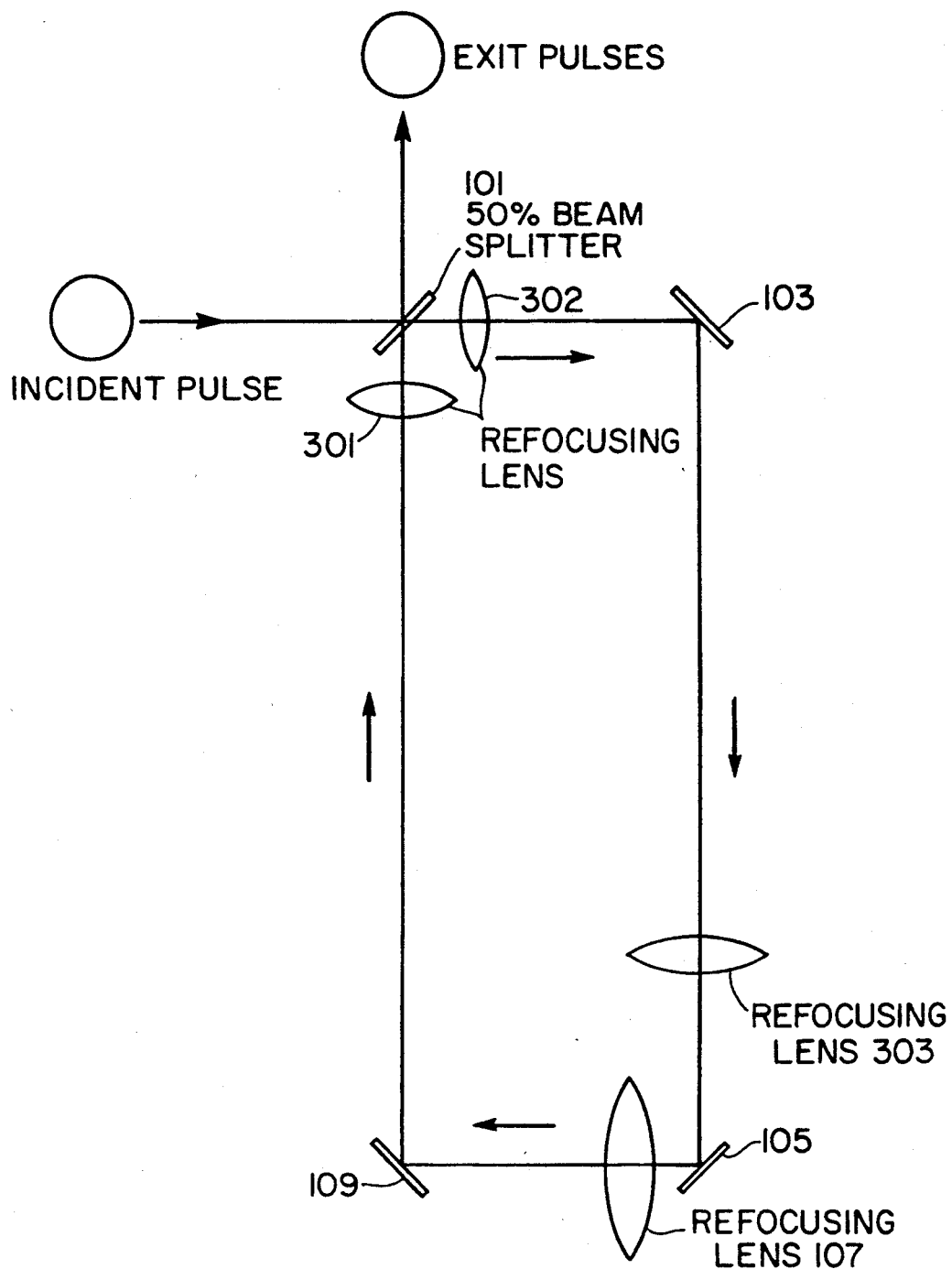
FIG. 5 shows an optical extender for converting a short pulse into a train of 3 to 4 pulses.

FIG. 5 shows an optical system which will convert a single incident pulse into a train of 3-4 pulses. The input light pulse is partially reflected and partially transmitted by the 50% beam splitter 101. The transmitted light is reflected back to the beam splitter where it again is partially reflected and partially transmitted. Light pulses will make at least two circuits of an delay optical path before being effectively reduced in amplitude. The optical path length is adjusted to produce a delay of at least 10–30 nanoseconds between light pulses. The optical delay path is comprised of mirrors 103, 105, 109 and refocussing lenses 107, 301, 302, 303. Lenses 107, 301, 302, 303 may be omitted and curved focusing mirrors substituted for flat mirrors 103, 105, 109 to accomplish the same purpose.

Figure 6:
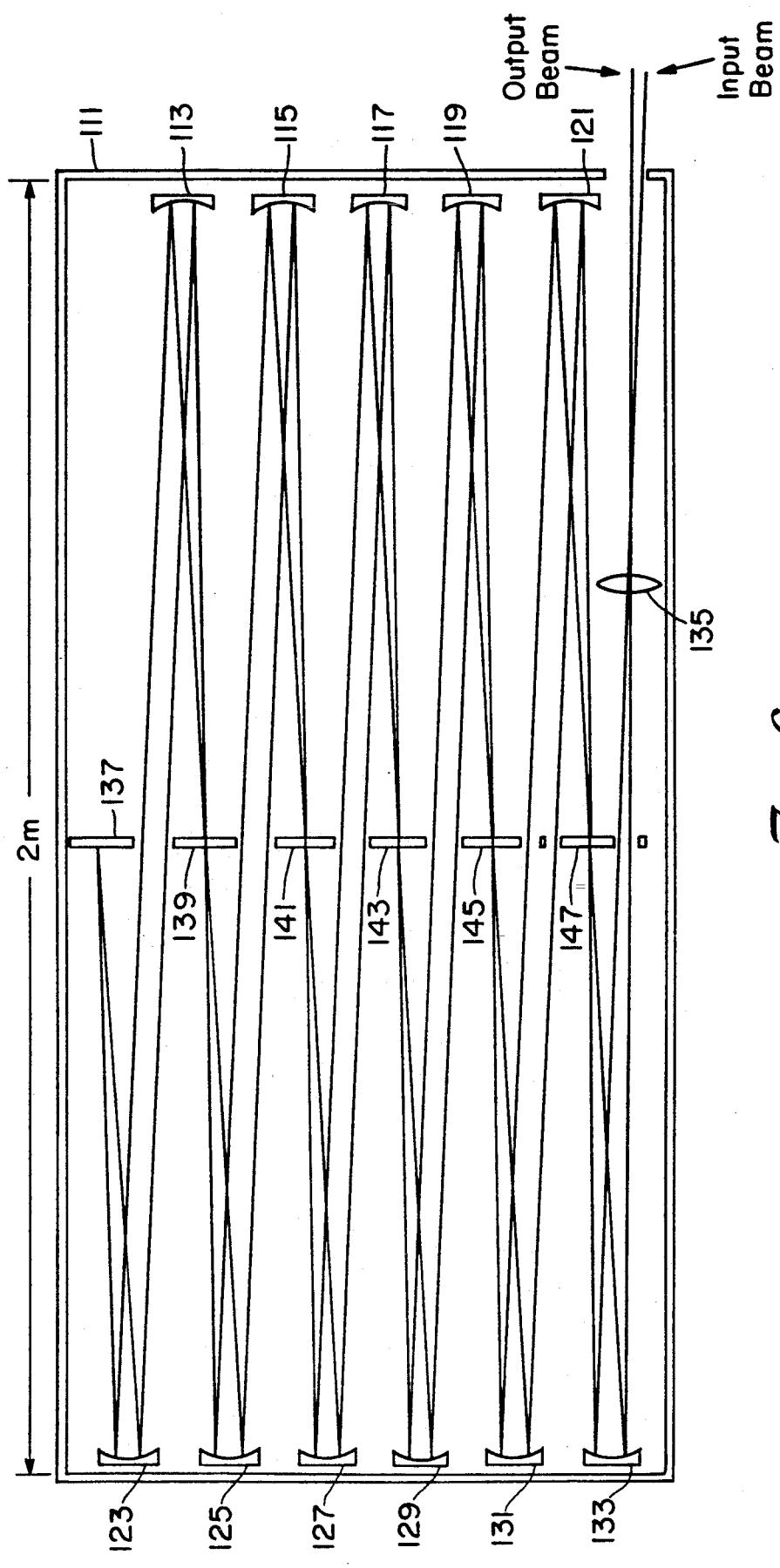
FIG. 6 illustrates another optical extender which can transform a single short pulse into a train of several pulses delayed by a given time interval.

FIG. 6 shows a commercially available optical device manufactured by Exitech Corporation for producing a train of light pulses delayed by a given time interval from a single short pulse. The lens 135 focuses the input beam at the midpoint of curved mirror 133, below beam splitter 147. The respective curved mirrors 113, 115, 117, 119, 121, 123, 125, 127, 129, 131, 133 focus the beam at the midpoint of the subsequent mirror. The beam is focused between the beam splitters 139, 141, 143, 145, 147 and collimated through the beam splitters 139, 141, 143, 145, 147. Mirror 137 is aligned with the beam splitters. The input and output beams are slightly off axis. Again, a train of output pulses is produced. Six pulses are produced of a length of 180 ns with each pulse having less than one sixth of the total energy of the input pulse.

Figure 7:
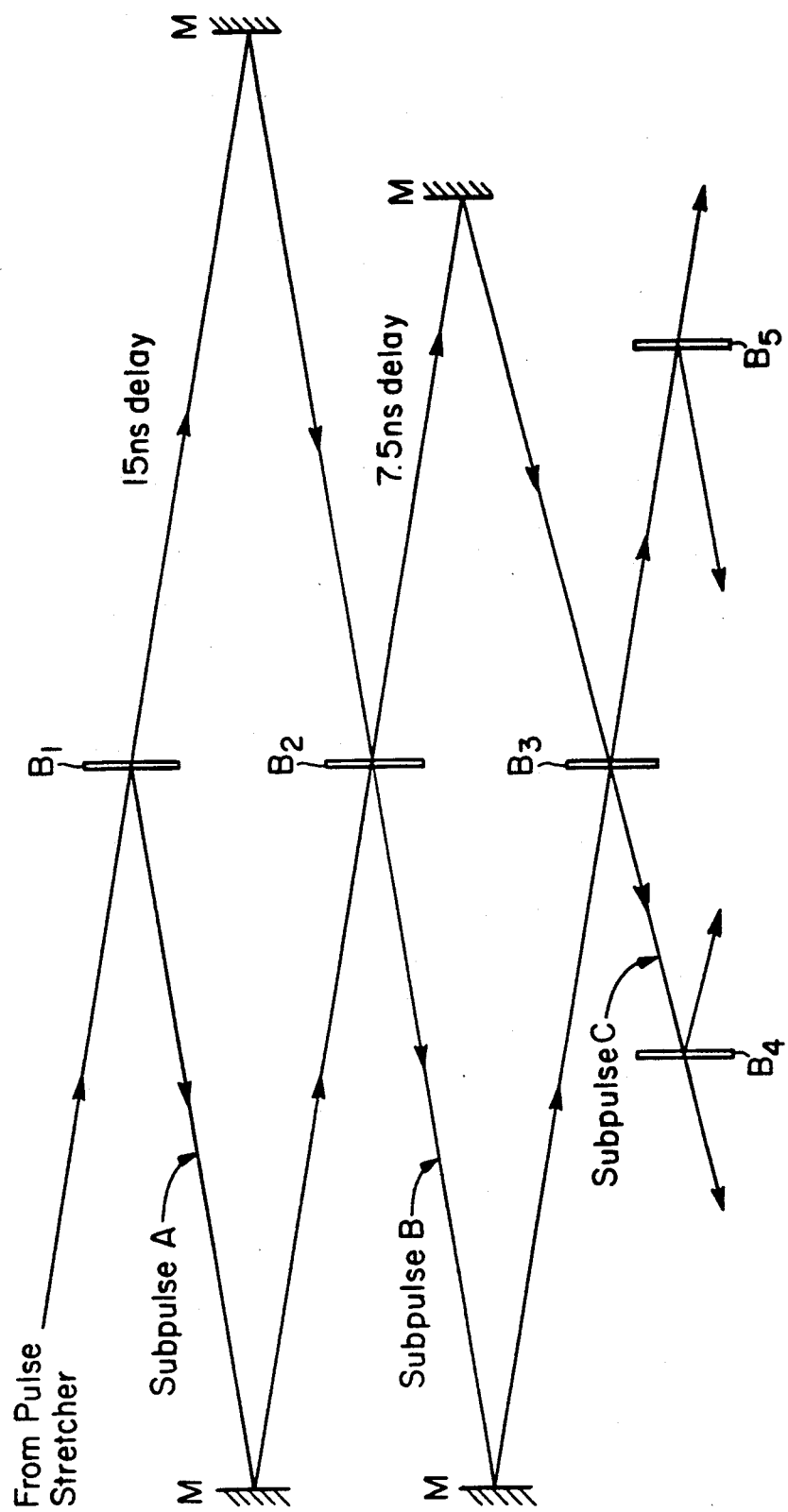
FIG. 7 shows a pulse broadening multiplexer which generates a plurality of overlapping pulses.

FIG. 7 shows a pulse filler/multiplexer. Multiple outputs of overlapped pulses are produced. A first beam splitter $B_1$ partially transmits and partially reflects the pulse. The transmitted pulse is delayed 15 ns by the optical path and is combined with the first pulse when it is transmitted by the second beam splitter $B_2$. The pulse is also reflected from the second beam splitter, delayed 7.5 ns and recombined at a third beam splitter $B_3$. As a result, two outputs of overlapping pulses are available at the third beam splitter $B_3$. The number of outputs can be doubled, or split, again by using further beam splitters $B_4$, $B_5$. The optical delays on either side of the beam splitters can be varied as needed to create the required fluence.

Figure 7A:
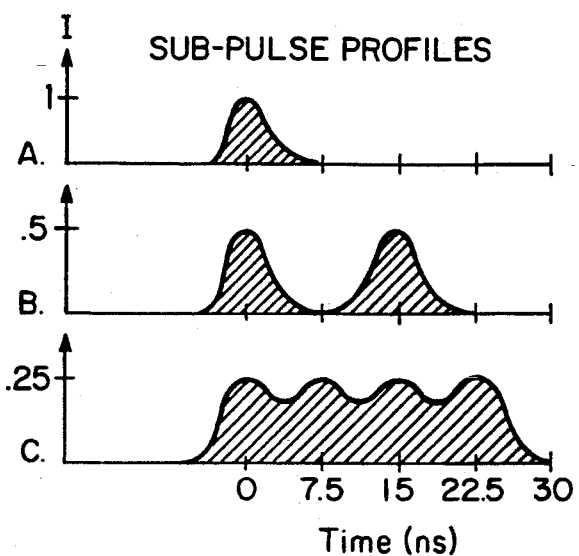
FIG. 7a shows the pulse outputs generated by the multiplexer.
Figure 8A:
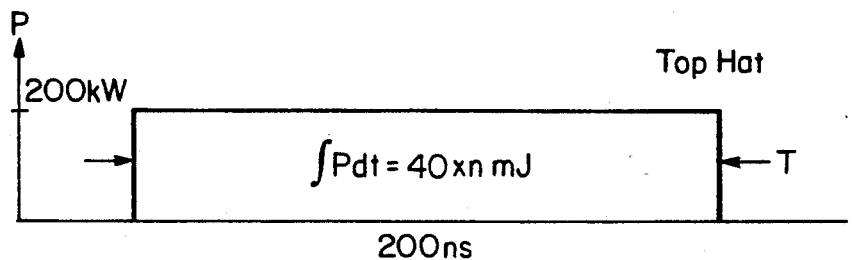
FIG. 8(a)-(e) and 9(a)-(c) show various laser pulse outputs which are effective for removing tissue.
Figure 8B:
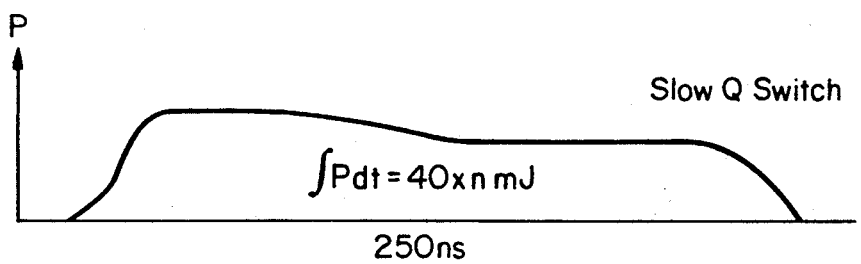
Figure 8C:
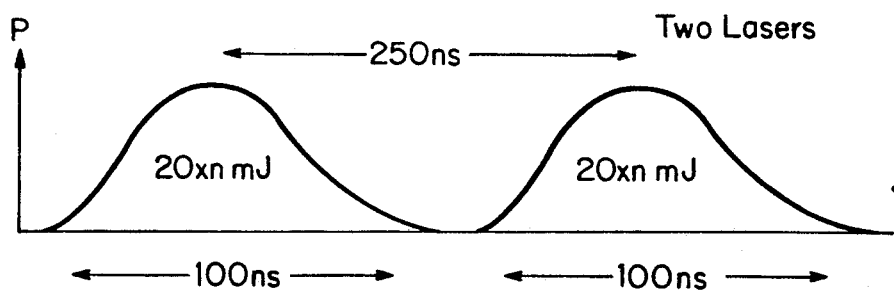
Figure 8D:
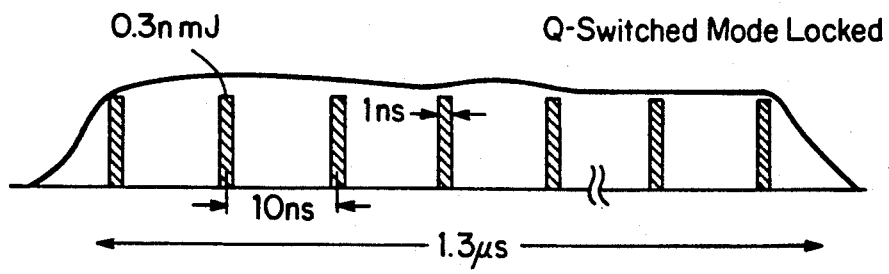
Figure 8E:
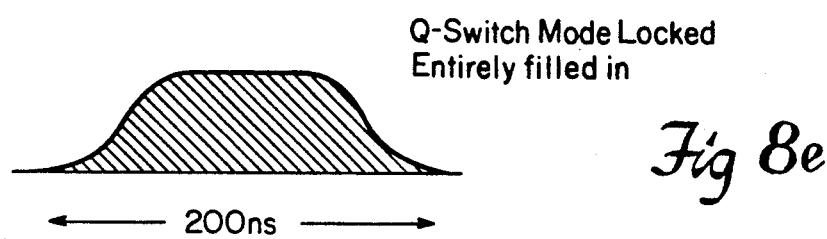

FIG. 7(a) illustrates the pulses which are developed at various stages in the pulse filler/multiplexer.

The filler/multiplexer of FIG. 7 can operate on the train outputs of the pulse extenders of the FIGS. 5 and 6 embodiments to produce a pulse of long duration. Alternatively, the output of overlapped pulses of FIG. 7 embodiment can be applied to the embodiments of FIGS. 5 and 6 to produce a long pulse.

The flat mirrors of FIG. 7 can be replaced by curved mirrors and corrective lenses to accomplish preservation of beam characteristics such as beam size and divergence.

As noted previously, many other lasers may be used. For example, a doubled Alexandrite or Ti:Sapphire laser. As infared optical fibers become available, ablation by lasers in the 3 $\mu$m region may become practical. Also, a long train of mode locked picosecond pulses from a solid state laser is one preferred method employing the system shown in FIGS. 5 and 7. Either long pulse solid state or long pulse gas lasers may be used.

Pulse stretching can be effected by active, as well as passive, devices. Also, more compact optical switching systems based on rotary, rather than linear, configurations which allow efficient uninterrupted illumination of any contiguous subset of fibers out of a circular catheter array, can be used.

Figure 10:
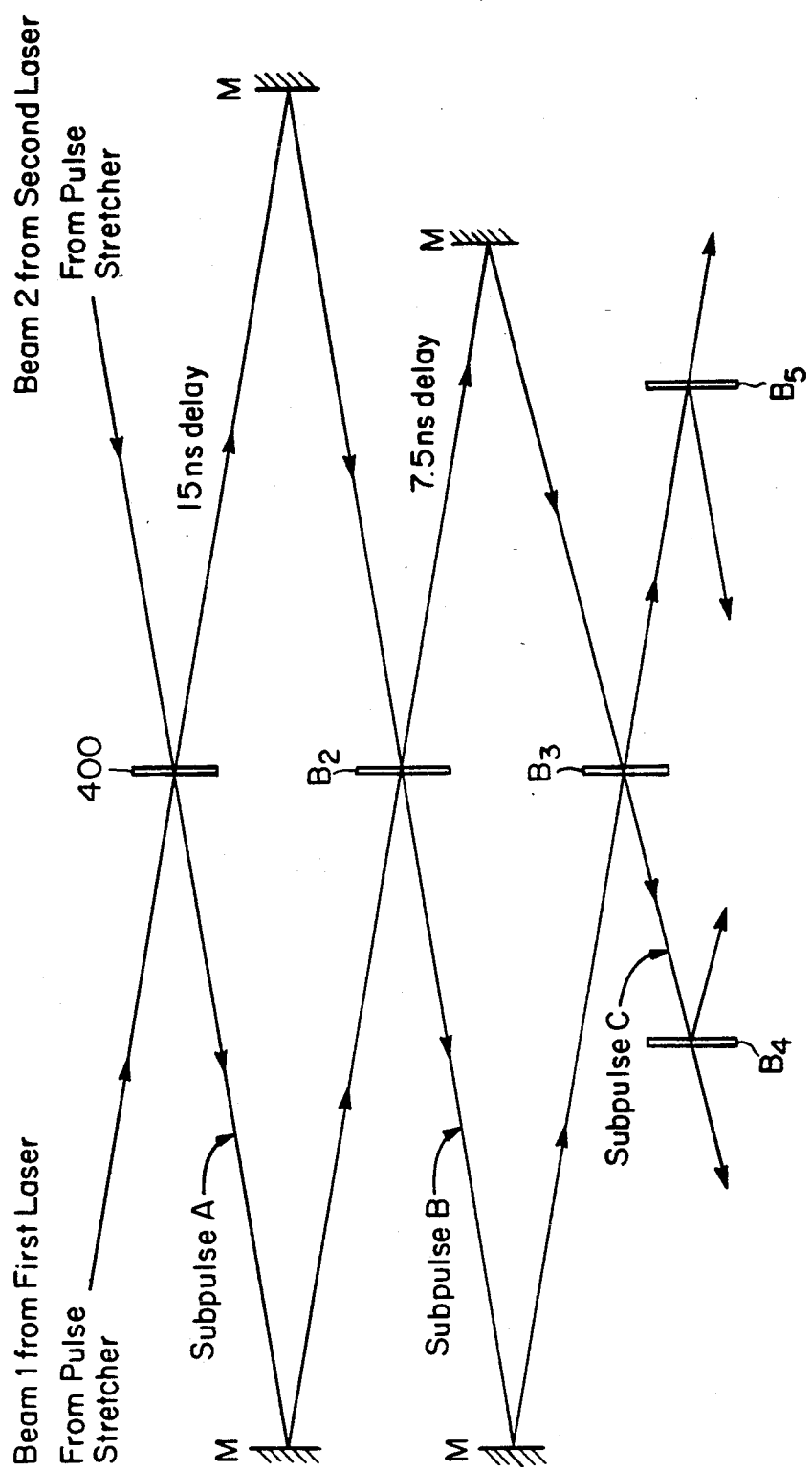
FIG. 10 shows a further embodiment of the pulse broadening multiplexer.

FIG. 10 shows another embodiment of the pulse broadening multiplexer. A Wollaston prism 400 combines the respective beams from two different plane polarized lasers. Accordingly, the number of pulses are doubled.

The wavelength of the laser is preferably in the range of 320 to 400 nm. This range is not mutagenic. Mutagenic effects peak at the 270–280 nm range. The range of 320–400 nm is above the vicinity of 308 nm where the incidence of cataracts peak. Moreover, losses due to optical distortion are minimal in this range. Also, the penetration depth of the beam is optimal in this range. This range avoids the incidence of spallation, in which large tissue chunks are ejected from the tissue surface by thermal expansion at a wavelength above 500 nm where tissue absorption is weak. Below 400 nm wavelengths, there is less penetration and less tissue damage. Also, at this range of 320–400 nonometers, the beam quality is more reliable. Moreover, in the ultraviolet range, lossy optics require a more powerful laser.

Plural pulses can be generated by combining pulses from two different lasers where the pulses from the respective lasers are separated in time by at least 100 ns. Thus, adequate fluence to remove tissue can be obtained without the use of optical extenders.

Figure 9A:
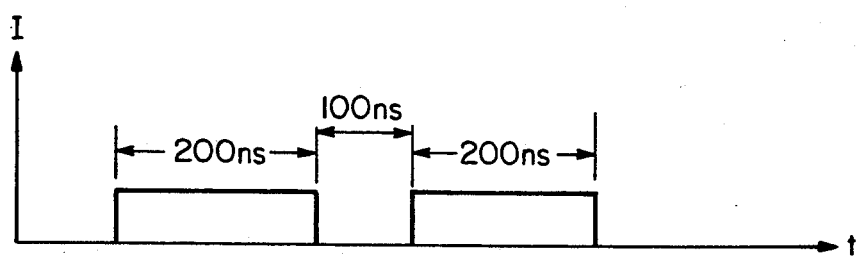
Figure 9B:
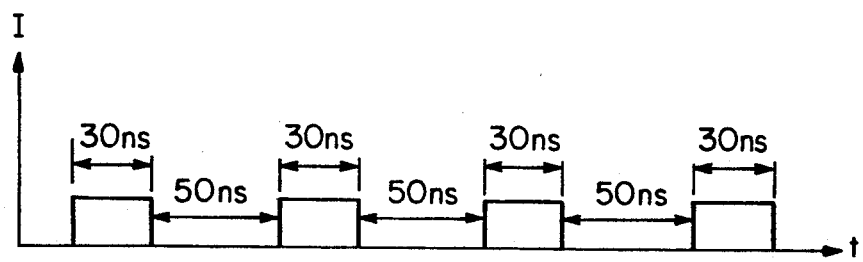
Figure 9C:
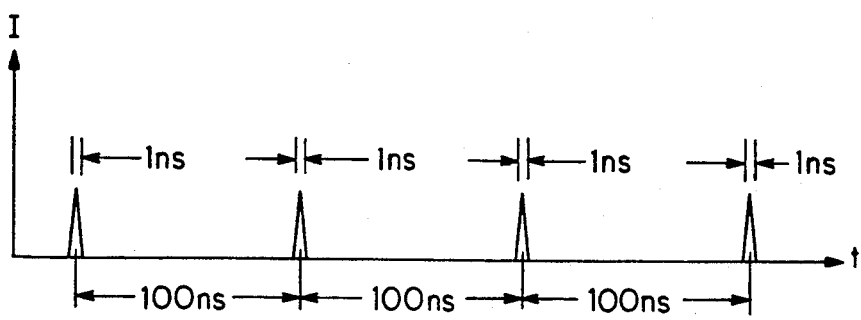

FIGS. 8 and 9 illustrate various laser output techniques which will create adequate fluence, or energy/$cm^2$, to remove tissue. FIGS. 8(a), 8(b), and 8(e), show a single pulse which produces a threshold fluence of 40 nm. Similarly, FIGS. 8(c) and (d) show plural output pulses which produce the same effect. FIG. 9 shows the variability in pulse duration and separation which will effect adequate fluence and thus proper tissue removal.

Figure 11:
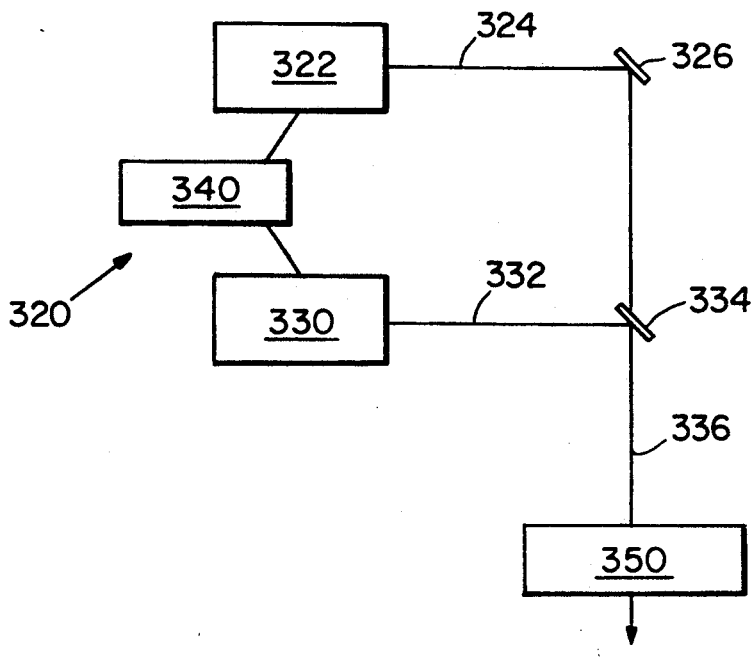
FIG. 11 illustrates a further embodiment of the laser subsystem to be employed in a sequenced pulse ablation procedure.

FIG. 11 illustrates another preferred embodiment of the ablation laser subsystem 237 of FIG. 4. This system 320 employs a first laser 322 which generates a beam 324 of pulsed laser radiation having a first wavelength, and a second laser 330 that produces a beam 332 having the same or a different second wavelength.

The beams 324 and 332 can be directed along a single path 336 using mirrors 326 and 334, respectively. The train of pulses can then be delivered into optical system 350 for coupling to the optical fiber selector and the catheter. Optical system 350 can be positioned in the optical circuit of the laser system to process either one or both beams 324 and 332. Optical system 350 can include a pulse stretcher or any other appropriate components as necessary and can be located at any appropriate position in the circuit.

As indicated previously, a critical factor in the use of two pulses in sequence to ablate a region of tissue is the temporal space that occurs between each pulse in the sequence. This is particularly true when the first pulse generates a transient response in the tissue which is critical to absorption of the following pulse. By coupling temporally adjacent pulses such that energy dissipation from the first pulse in the tissue is limited before the second pulse arrives provides for increased effectiveness in the ablation process. For example, two pulses that individually do not have enough energy to result in tissue removal, i.e. they do not exceed the fluence threshold for ablation, can result in ablation when they are delivered to the tissue to be removed within a certain period. In addition, the duration of the period between pulses can affect the depth of the hole or crater that is created in the tissue. Thus, control must be exercised over the period between pulses to provide for proper coupling of a pulse sequence to maximize ablation.

To achieve proper control over the time period between coupled pulses a number of different mechanisms can be used depending upon the type of control required. One alternative is to trigger both lasers 322 and 330 of FIG. 11 with control circuit 340 at the same time and insert a delay line in the optical path of one of the beams 324 and 332 to provide for proper temporal spacing between the pair of pulses. Control circuit 340 can alternatively include a variable delay or a microprocessor programmed to provide proper pulse spacing and beam intensity. The subsystem of FIG. 11 can be used with the diagnostic, display, control and catheter subsystems shown in FIG. 4. In particular, control circuit 340 can operate in response to the diagnostic subsystem 201.

The laser ablation system 320 illustrated in FIG. 11 has particular use when the beams 324 and 332 have different wavelengths.

Possible mechanisms involved in the alteration of light propagation of the tissue in response to the first wavelength pulse include photochemical, thermal, electrical and vibrational processes. These processes can be transient (reversible) or, in other cases, permanent (irreversible). For example, thermal heating of tissue can cause protein denaturation that is either reversible or irreversible and which can alter light scattering and absorption properties. These changes alter the attenuation of light as it propagates through tissue. Electronic and vibrational changes can alter the population of energy levels within tissue molecules. For example, the transfer of population from the ground state to a long lived triplet state can alter the absorption of the material. Photochemical changes can give rise to new molecular components with increased absorption properties.

Figure 12:
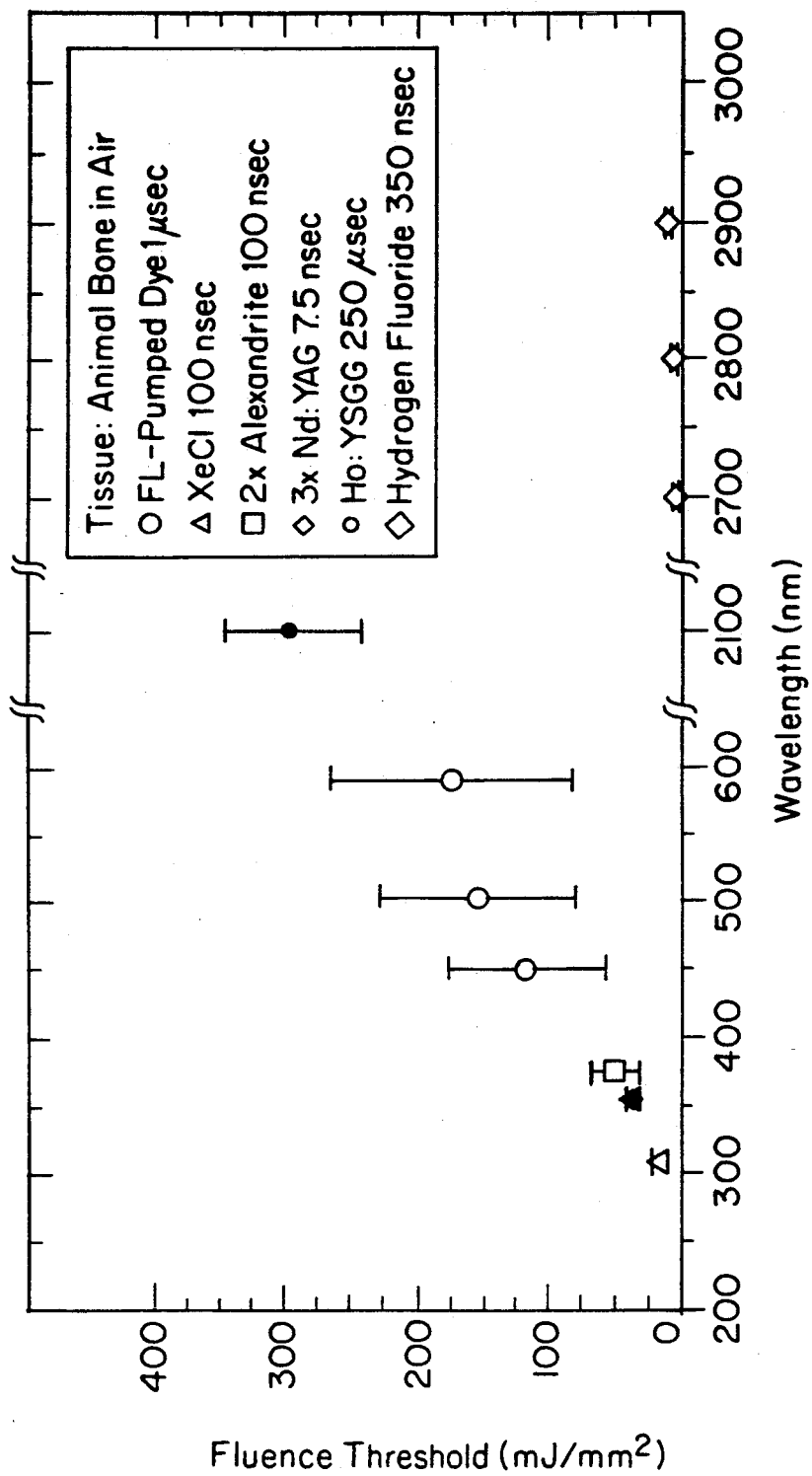
FIG. 12 illustrates the fluence thresholds that are necessary to provide ablation using various lasers.

To assist in understanding the significance of the following two color ablation procedures, it is helpful to know the fluence thresholds provided by various types of lasers operating at different wavelengths that are suitable for tissue ablation. FIG. 12 illustrates the fluence thresholds on animal bone in air for a pumped dye laser having 1 microsecond long pulse, a xenon cloride laser with a 100 nanosecond pulse, a frequency doubled Alexandrite laser with a 100 nanosecond pulse, a frequency triped ND:YAG laser with a 7.5 nanosecond pulse, a HO:YSGG laser with a 250 microsecond pulse and a Hydogen Fluoride laser with a 350 nanosecond pulse. It is important to realize that the fluence threshold is dependent upon the size of the spot generated by the beam. The significance of the present invention is that longer wavelength lasers emitting in the range between 400 and 3000 nm can be used with a short wavelength laser to produce an effective laser ablation system.

Figure 13:
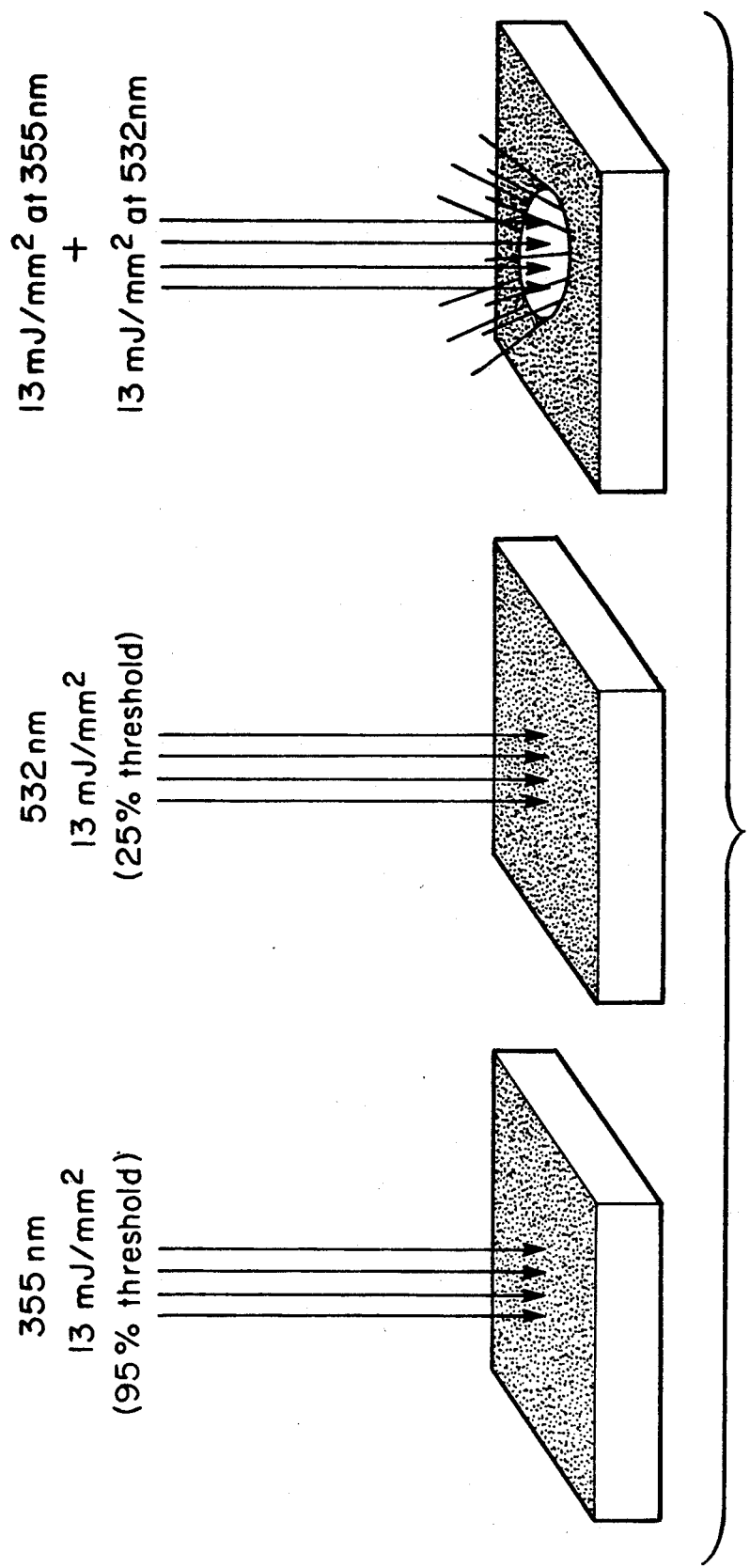
FIG. 13 illustrates the particular wavelengths and energy levels of a particular two color ablation process.

In particular, the fluence threshold on animal bone in air for a frequency tripled ND:YAG laser light (355 nm) of a selected spot size has a fluence threshold of about 15 mj/$mm^2$. For a frequency doubled ND:YAG (532 nm), the fluence threshold (which, again is spot size dependent) for ablation is about 50 mj/$mm^2$. It has been found that the coupling of a longer wavelength pulse (532 nm) below the threshold fluence with a previously delivered 355 nm, that is also below the fluence threshold, results in the substantially char free ablation of bone if the pulse separation is near or below 1 microsecond. This fact is illustrated in FIG. 13 where two 13

MJ/Mm² pulses were coupled to produce ablation of the sample.

As the longer wavelength pulse can be transmitted by optical fibers better than shorter wavelengths, a substantial improvement in ablation effectiveness can be realized if the short wavelength pulse can be used to prepare the tissue, and the longer wavelength can be effectively absorbed to complete an ablation cycle. The proper selection of pairs of wavelengths involves the use of a first wavelength that improves the absorption of the tissue at the second wavelength.

Figure 14:
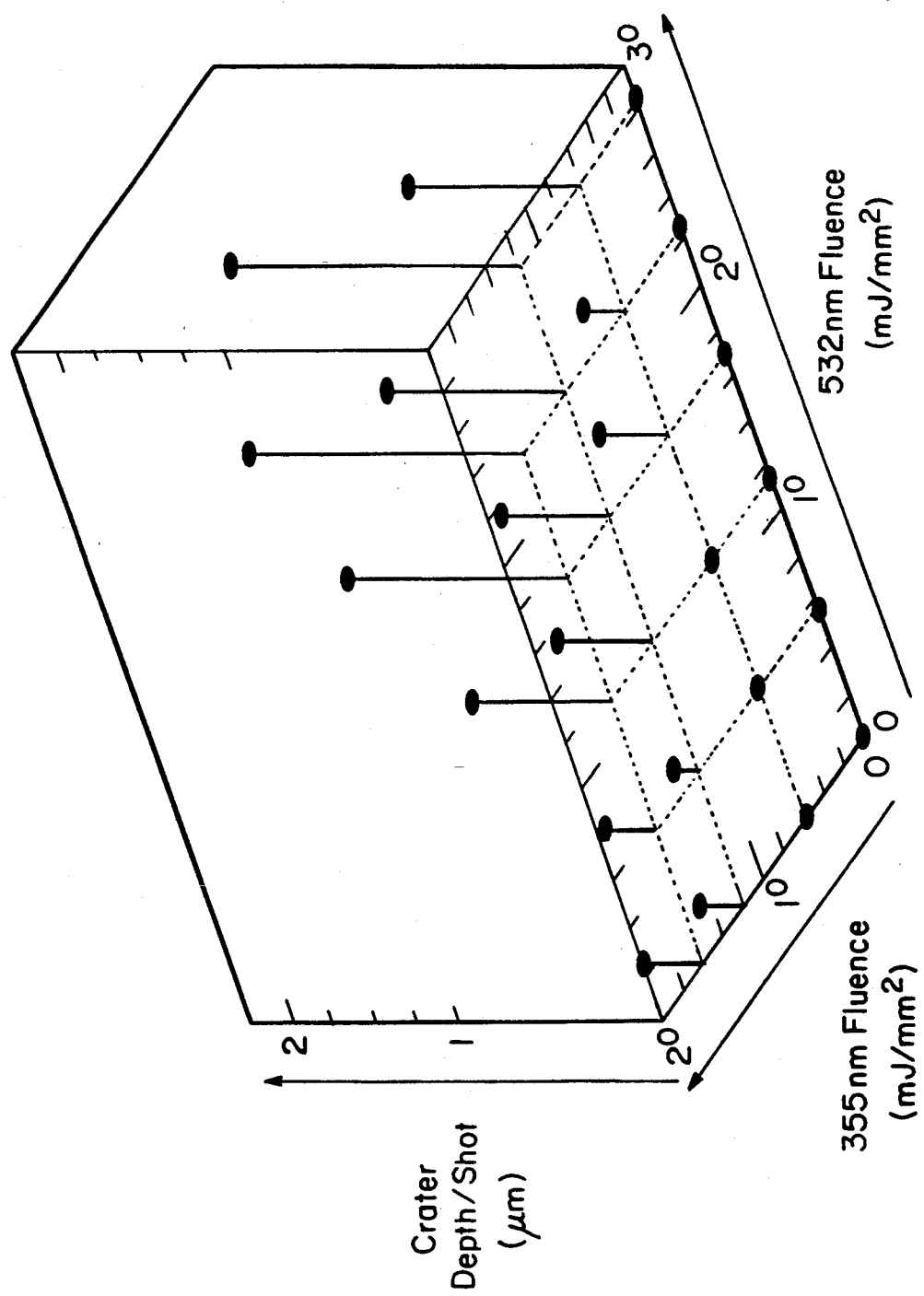
FIG. 14 is a three-dimensional graphical representation illustrating crater depth in a tissue sample as a function of fluence of the two colors or wavelengths being employed.

As shown in the three-dimensional graph of FIG. 14 in which two pulses of different wavelengths were delivered to animal bone with a pulse separation of 100 nsec, where the first shorter wavelength pulse (355 nm) has a fluence at or near zero, no ablation occurs with the longer wavelength at fluences up to 30 mj/mm². However, where the first pulse has a fluence sufficient to prepare the tissue, effective controlled ablation will result. This synergy between two or more wavelengths of light is optimized for each type of tissue to be removed. Both subthreshold energy levels, and superthreshold energy levels can be used for one or both pulses in a pulse pair to control the depth of tissue being removed.

In an alternative embodiment an excimer laser such as xenon flouride laser emitting at 351 nm or other known excimer lasers operating at shorter wavelengths or a frequency tripled ND:YAG laser emitting at 355 nm (or quadripled at 266 nm) can be used to prepare the tissue, and a longer wavelength laser, such as a holmium doped solid state laser emitting at 2100 nm can be used to complete an ablation cycle. The short wavelength pulse alters the attenuation coefficient of the tissue resulting in a significantly reduced absorption depth for the second pulse.

The optimal choice of pulse pairs depends upon the type of tissue, the wavelengths of the pulses within the sequence, and the amount of tissue to be removed with each pulse sequence. As the type of tissue being removed can vary after a given amount of tissue is removed, the energy from one or both lasers or the temporal separation of pulses within a sequence can be altered to increase or decrease the rate of ablation as desired.

Figure 15:
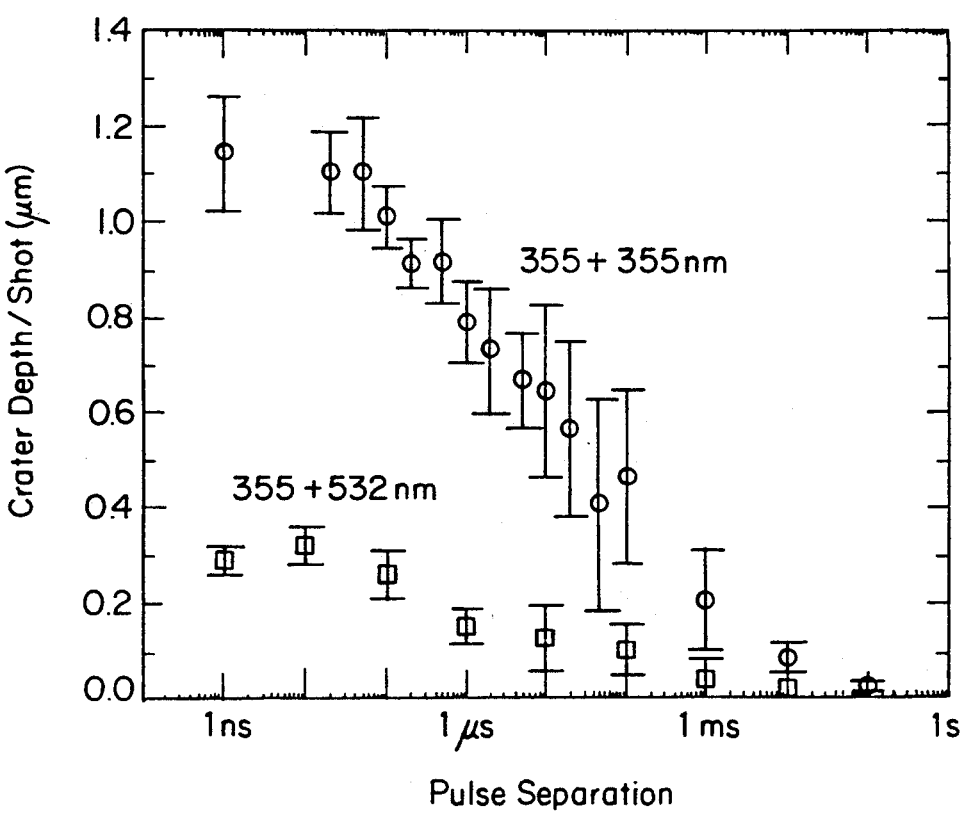
FIG. 15 is a graphical illustration of crater depth in bone tissue versus pulse separation of sequenced pulse ablation using one and two wavelengths.

FIG. 15 illustrates the effect of pulse separation on crater depth for both single wavelength and multi-wavelength pulse sequences. For both cases the optimal pulse separation occurs in the range below 1 microsecond as the mechanism used to alter tissue absorption caused by the first pulse is highly transient. Note that the fact that the two color procedure produces shallower crater depths per shot in this graph is not representative of their relative effectiveness. This graph does not include other effects that operate to increase the effectiveness of the two color process in surgical applications. These effects include the ease of use and reduced optical losses that occur when using longer wavelength lasers.

Figure 16:
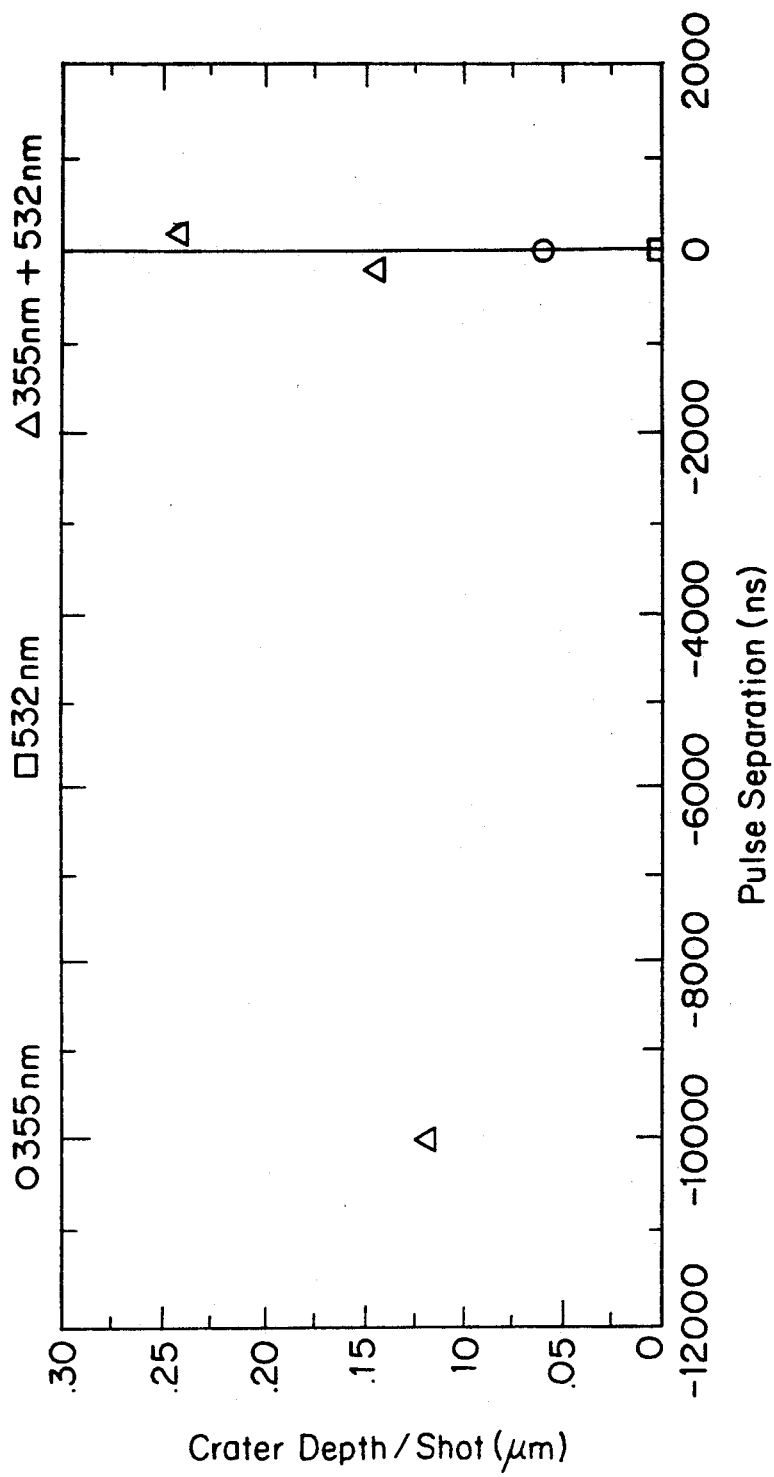
FIG. 16 is a graphical illustration of crater depth in bone tissue for selected pulse pairs.

The importance of the sequence of pulses of different wavelengths is illustrated by FIG. 16 in which crater depth/per shot is plotted as a function of pulse separation. When a green pulse (532 nm) alone is used having a fluence of 45 MJ/Mm² it produced no observable ablation. A single blue pulse (355 nm) resulted in a small crater. A green pulse followed 10 microseconds later by a blue pulse resulted in a slightly larger crater, and where the blue pulse follows by 200 ns, the crater depth/shot is about 0.147 microns. However, when a blue pulse is used to prepare the tissue and is followed 200 ns later by a green pulse, the crater depth is substantially greater than all of the other wavelengths or illustrated wavelengths pairs. This data illustrates the importance of the order in which the wavelengths are used as the blue pulse operated to prepare the tissue for absorption of the green pulse far more effectively. For the purposes of this application a substantial reduction in the depth of propagation of the second pulse in the tissue is at least one-half the penetration depth then would normally occur without preparation by the first pulse.

EQUIVALENTS

Those skilled in the art will recognize, or be able to ascertain, using more than routine experimentation, many equivalents to the specific embodiments of the invention described herein.

These and all other equivalents are intended to be encompassed by the following claims.

We claim:

1. A method of removing material from a surgical site comprising:
   irradiating a portion of material with a first pulse of light having a first wavelength and pulse duration to prepare the material without creating a plasma and without removal of material by the first pulse of light; and
   irradiating the portion with a second pulse of light having a second wavelength longer than the first wavelength and within a selected period following the first pulse to remove the portion of material from the surgical site, a depth of propagation of the second pulse within the material being substantially reduced by the first pulse during the selected period.

2. The method of removing material from a vascular lumen of claim 1 wherein the second pulse irradiates cancerous material at the site within a selected period following the first pulse, the period having a duration of less than 1 millisecond.

3. The method of removing material of claim 1 wherein the first wavelength is a selected harmonic of an output beam from a laser.

4. The method of removing material of claim 3 wherein the second wavelength is a further selected harmonic of the output beam from the laser.

5. The method of removing material of claim 1 wherein the first wavelength is in a range between 300 nm and 400 nm.

6. The method of removing material of claim 1 wherein the second wavelength is in a range between 400 nm and 3000 nm.

7. The method of removing material of claim 1 wherein the irradiating steps comprise irradiating the material including atherosclerotic plaque located within an arterial lumen of a patient with a Nd:YAG laser.

8. A laser angiosurgery system for removing material including plaque from a site within an arterial lumen of a patient comprising:
   a fiber-optic catheter having a cross-sectional area to permit insertion of the catheter into an arterial lumen of a patient;
   a laser system providing first and second wavelengths of light that can be coupled to a proximal end of the catheter to deliver laser radiation to a site in the lumen and further comprising:

a control system connected to the laser system such that the laser system generates a first pulse of radiation having the first wavelength and a second pulse of radiation having the second wavelength, the first and second pulses being transmitted through the catheter that delivers the first and second pulses to a region of material including plaque at the site within a selected period of time such that the first pulse irradiates the material without creation of a plasma to alter an optical absorption characteristic of the material upon delivery of the second pulse to the material, the first and second pulses acting in combination to deliver sufficient energy to the region to remove material including plaque at the site in the lumen.

9. The system for removing material from a site of claim 8 wherein the laser system comprises a Nd:YAG laser.

10. The system for removing material from a site of claim 8 wherein the first wavelength is in the range between 300 nm and 400 nm.

11. The system for removing material from a site of claim 8 wherein the second wavelength is in the range between 400 nm and 3000 nm.

12. The system for removing material from a site of claim 8 wherein the second pulse irradiates the tissue within a selected period following the first pulse, the period having a duration of less than 1 millisecond.

13. The system for removing material from a site of claim 8 wherein the first wavelength is a selected harmonic of an output beam from a laser and the second wavelength is a further selected harmonic of the output beam from the laser.

14. The system for removing material from a site of claim 8 wherein the first wavelength has an ultraviolet wavelength and the second wavelength has a visible wavelength.

15. The system for removing material from a site of claim 8 wherein the first wavelength has an ultraviolet wavelength and the second wavelength has an infrared wavelength.

16. A system for removing material from a site comprising:

a first laser providing a first wavelength of radiation;

a second laser providing a second wavelength of radiation that is longer than the first wavelength;

a control system connected to the first laser and the second laser to generate a first pulse of radiation having the first wavelength and a second pulse having the second wavelength, the first and second pulses being received by an optical system that delivers the first and second pulses to a region of the material within a selected period of time such that the first pulse irradiates the material without creating a plasma and without removing material from the site to alter an optical absorption characteristic of the material upon delivery of the second pulse to the material which removes material from the site.

17. The system for removing material from a site of claim 16 wherein the first or second laser comprises a Nd:YAG laser.

18. The system for removing material from a site of claim 16 wherein the first wavelength is in the range between 300 nm and 400 nm and the second wavelength is in the range between 400 nm and 3000 nm.

19. The system for removing material from a site of claim 16 wherein the second pulse irradiates the tissue within the selected period following the first pulse, the period having a duration of less than 1 millisecond.

20. The system for removing material from a site of claim 16 wherein the second pulse has an energy density sufficient to remove atherosclerotic plaque from the site.

* * * * *